(12) United States Patent
Harding

(10) Patent No.: US 6,725,467 B2
(45) Date of Patent: Apr. 27, 2004

(54) RIP OFF SHEET MOUNTING DEVICE FOR GOGGLES WITH ROLL STRIP MECHANISM AND RIP OFF SHEETS

(76) Inventor: Lester M. Harding, 13 Downing Avenue, Guildford, Surry (GB), GU2 7SY (*) Notice: Subject to any disclaimer, the term of this patent is extended or adjusted under 35 U.S.C. 154(b) by 74 days.

(21) Appl. No.: 10/067,461

(22) Filed: Feb. 4, 2002

(65) Prior Publication Data

US 2002/0104154 A1 Aug. 8, 2002

(30) Foreign Application Priority Data

Feb. 5, 2001 (GB) .............................................. 0102828

(51) Int. Cl.[7] .................................................. A61F 9/02
(52) U.S. Cl. .............................................. 2/435; 2/438
(58) Field of Search .......................... 2/424, 434, 436, 2/438, 435, 422; 351/47

(56) References Cited

U.S. PATENT DOCUMENTS

| | | | | |
|---|---|---|---|---|
| 4,138,746 A | * | 2/1979 | Bergmann | ..................... 2/424 |
| 4,428,081 A | * | 1/1984 | Smith | ............................. 2/438 |
| 4,528,701 A | * | 7/1985 | Smith | ............................. 2/438 |
| 4,542,538 A | | 9/1985 | Moretti et al. | |
| 4,748,697 A | | 6/1988 | Hodnett | |
| 5,163,185 A | | 11/1992 | Hodnett | |
| 5,592,698 A | * | 1/1997 | Woods | ........................... 2/424 |
| 6,388,813 B1 | * | 5/2002 | Wilson et al. | .............. 359/630 |
| 6,416,177 B1 | * | 7/2002 | Gibson | ........................ 351/41 |

\* cited by examiner

*Primary Examiner*—Katherine Moran
(74) *Attorney, Agent, or Firm*—Ware, Fressola, Van Der Sluys & Adolphson LLP

(57) ABSTRACT

A projection 1 mounted onto, or produced as an integral part of a roll holder cover 3 which is part of eye safety wear (goggles) suitable for use in motocross and other activities, which enables the use of both rip off sheets and roll on strips on a single set of goggles in a single use. Two roll holder covers are mounted to each side of the goggles. Each projection has an upstanding tab 18 for receipt of a rip off sheet which spans the corresponding two projections.

14 Claims, 1 Drawing Sheet

RIP OFF SHEET MOUNTING DEVICE FOR GOGGLES WITH ROLL STRIP MECHANISM AND RIP OFF SHEETS

TECHNICAL FIELD

This invention relates to a design of eye safety wear (goggles) for use in motocross and other similar sports which facilitates the use of both rip off sheets and a roll on strip mechanism to provide the user with clearer vision for a longer period.

BACKGROUND OF THE INVENTION

Those who take part in motocross experience the problem of not being able to maintain clear vision throughout the length of a race. The current goggles available give the option of using either rip off sheets or a roll on strip, but not both, a separate set of goggles being used depending on the choice of vision clearance.

The rip off sheets are limited to around four at the start of the race. If a greater number is used then basic vision becomes obscured. A rider will often find that this limited number results in the surface of the goggles being very dirty and difficult to see through for much of the end part of the race, all the rip off sheets having been used.

The standard roll on mechanism is a thin strip across the goggles surface, which is transferred from a roll on one side of the goggles to the other by the rider throughout the course of a race. This roll on strip will normally last the race length but can only provide a narrow field of clear vision.

The current design for rip off sheets is that these are attached to the goggles on small projections from the surface of the goggles. These projections prevent the use of rip off sheets with a roll on strip as the roll on strip catches on the projections.

SUMMARY OF THE INVENTION

This invention adds to the existing eyewear used, which would normally be purchased with a roll on strip, by adding onto the roll holder cover a projection suitable for attaching rip off sheets, and so facilitating the use of both methods of clearing the goggles surface in a single set of goggles.

BEST MODE FOR CARRYING OUT THE INVENTION

Figure 1:
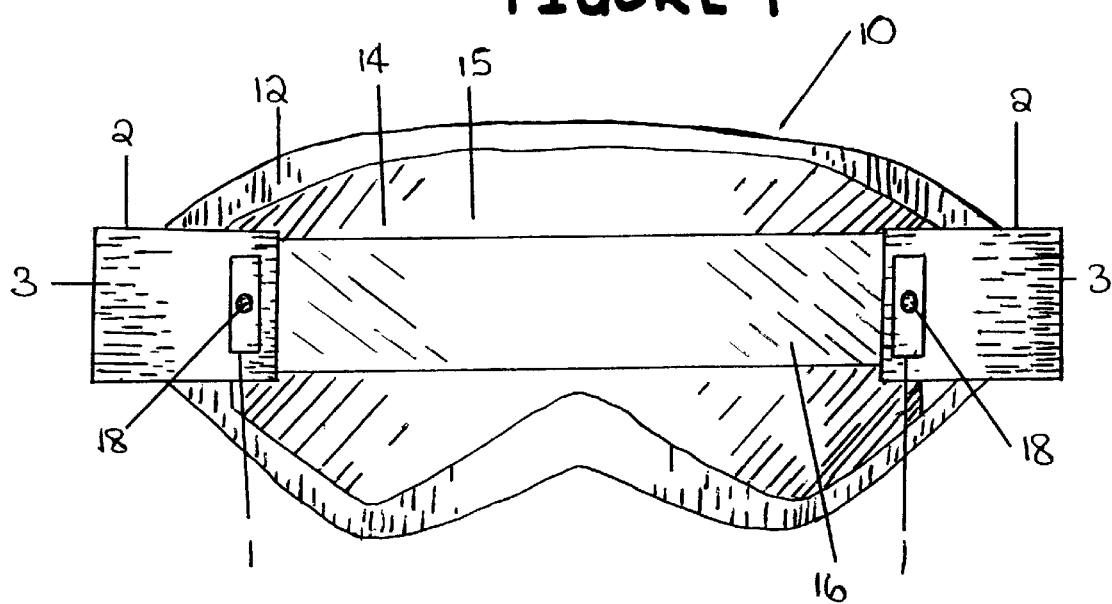
FIG. 1 is a front view of a set of goggles with roll holders on either side of the goggles, illustrating the projections of the present invention.
Figure 2:
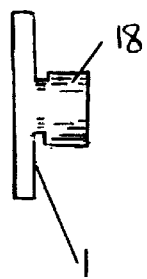
FIG. 2 is a side view of the projection according to the present invention.

As seen in FIGS. 1 and 2, a set of goggles 10 has an outer frame 12 and a region 14, covered with a transparent lens 15. In sports such as motocross, the goggles quickly becomed covered with mud and the like, as such material is kicked into the air by adjacent bikers. Roll holders 2 and 2' with outer covers 3 and 3' are sometimes attached to the goggles. One of the roll holder 2' is initially filled with a transparent roll of material 16 which extends to the other roll holder 2. During a race or the like, the biker can cause the material to advance from the first holder 2' to the other holder 2, as mud builds on the exposed portion of material 16.

A disadvantage of roll holders is that the material 16 has a relatively narrow width as compared to region 14 corresponding to lens 15 of the goggles. Therefore mud quickly can build up on that portion of lens 15 which is not overlayed with material 16. This mud buildup greatly restricts the biker's field of view.

Rip off sheets have been used with some success as an alternative to the roll material. Rip off sheets are typically attached to goggles that do not have roll holders attached. The problem with rip off sheets is that there is a practical limit to the number of sheets that can be layered over each other at the start of an biking event. This number is typically four or five sheets. More than this number of sheets causes too much obscuring of vision due to the cumulative thickness of the sheets. As a result, there generally are not enough rip off sheets to provide clear vision toward the end of an event.

As seen in FIGS. 1 and 2, projections 1 can be mounted on to the roll holder covers 3 and 3', or manufactured as an integral part of the roll holder covers. If mounted to the roll holders, such mounting can be achieved by glue, sonic welding or the like. If the projections are integral with the roll holders, the same material as the roll holder would be used. If produced as a separate part it can be produced in any suitable impact resistant material such as polycarbonate, ABS, butyl, polypropylene copolymer, rubber, transparent thermoplastic or other materials suitable for absorbing impact without being dislodged or suffering structural failure.

The rip off sheets are attached to the upstanding tab 18 of each projection 1. The sheets (not shown) typically have the same general shape as lens 15 and therefore provide greater protection in terms of viewing area as compared to strip material 16.

In practice, the biker tears off the rip off sheets during the early part of an event where the greatest amount of mud is generally sprayed into the air by nearby bikers. After the rip off sheets have been removed, the biker uses the roll holder material to keep a clear field of vision during the latter stages of the event where less mud is sprayed into the air due to normal greater separation of bikers at the latter stages of the event. Thus the advantage of the large area rip off sheets is combined with the more unlimited supply of material of the roll holder in a manner not heretofore achievable.

What is claimed is:

1. A rip off sheet mounting device for use with a single set of goggles, comprising:

a pair of roll holders dimensioned for attachment to the set of goggles, the roll holders for receipt of a roll of strip material, each roll holder having an outer cover; and a pair of projections mounted respectively to the pair of roll holder covers so as to extend from the roll holder covers, the projections each dimensioned for receipt of rip off sheets.

2. A rip off sheet mounting device as defined in claim 1, wherein each projection is fabricated from an impact resistant material.

3. A rip off sheet mounting device as defined in claim 2, wherein the impact resistant material from which the projection is fabricated is chosen from the group consisting of polycarbonate, ABS, butyl, polypropylene copolymer, rubber, and transparent thermoplastic.

4. A rip off sheet mounting device as defined in claim 3, wherein each projection includes an upstanding tab dimensioned for receipt of said rip off sheets.

5. A rip off sheet mounting device as defined in claim 4, wherein each tab is specifically dimensioned for receipt of up to approximately five rip off sheets.

6. A rip off sheet mounting device as defined in claim 2, wherein each projection includes an upstanding tab dimensioned for receipt of said rip off sheets.

7. A rip off sheet mounting device as defined in claim 6, wherein each tab is specifically dimensioned for receipt of up to approximately five rip off sheets.

8. An improved set of goggles comprising:

a set of goggles having an outer frame defining an interior region, the interior region covered by a transparent lens;

a pair of roll holders mounted to the set of goggles, the roll holders for receipt of a roll of strip material, each roll holder having an outer cover; and a pair of projections mounted respectively to the pair of roll holder covers, the projections each dimensioned for receipt of rip off sheets.

9. An improved set of goggles as defined in claim 8, wherein each projection is fabricated from an impact resistant material.

10. An improved set of goggles as defined in claim 9, wherein the impact resistant material from which the projection is fabricated is chosen from the group consisting of polycarbonate, ABS, butyl, polypropylene copolymer, rubber, and transparent thermoplastic.

11. An improved set of goggles as defined in claim 10, wherein each projection includes an upstanding tab dimensioned for receipt of said rip off sheets.

12. An improved set of goggles as defined in claim 11, wherein each tab is specifically dimensioned for receipt of up to approximately five rip off sheets.

13. An improved set of goggles as defined in claim 8, wherein each projection includes an upstanding tab dimensioned for receipt of said rip off sheets.

14. An improved set of goggles as defined in claim 13, wherein each tab is specifically dimensioned for receipt of up to approximately five rip off sheets.

* * * * *